United States Patent [19]

Kelleher et al.

[11] Patent Number: 5,567,724
[45] Date of Patent: Oct. 22, 1996

[54] ALKALINE AND ACID PHOSPHATASE INHIBITORS IN TREATMENT OF NEUROLOGICAL DISORDERS

[75] Inventors: Judith A. Kelleher, Irvine; David D. Eveleth, Mission Viejo, both of Calif.

[73] Assignee: Cortex Pharmaceuticals, Inc., Irvine, Calif.

[21] Appl. No.: 252,109

[22] Filed: Jun. 1, 1994

Related U.S. Application Data

[63] Continuation-in-part of Ser. No. 71,281, Jun. 1, 1993, abandoned.

[51] Int. Cl.$^6$ ............................................. A61K 31/38
[52] U.S. Cl. ................................. 514/368; 514/568
[58] Field of Search ................................. 514/372, 263, 514/410, 368, 568

[56] References Cited

U.S. PATENT DOCUMENTS

| | | | |
|---|---|---|---|
| 4,701,407 | 10/1987 | Appel | 435/4 |
| 4,727,041 | 2/1988 | Aroonsakul | 436/8 |
| 4,753,964 | 6/1988 | Horrobin | 514/558 |
| 4,758,430 | 7/1988 | Sabin | 424/94.1 |
| 4,810,497 | 3/1989 | Horrobin | 424/153 |
| 4,837,164 | 6/1989 | Glick | 436/88 |
| 4,874,694 | 10/1989 | Gandy | 435/15 |
| 4,883,876 | 11/1989 | Nakatsuka | 546/81 |
| 4,939,124 | 7/1990 | Cacabelos | 514/12 |
| 4,939,175 | 7/1990 | Ukai | 514/646 |
| 4,973,591 | 11/1990 | Selkirk | 514/255 |
| 5,017,470 | 5/1991 | Aroonsakul | 435/4 |
| 5,063,220 | 11/1991 | Selkirk | 514/161 |
| 5,100,654 | 3/1992 | Ali-Khan | 424/7.1 |
| 5,135,847 | 8/1992 | Hoke | 435/5 |
| 5,151,508 | 9/1992 | Salbaum | 536/27 |
| 5,200,324 | 4/1993 | Navaratnam | 424/153 |
| 5,206,260 | 4/1993 | Hichens | 514/411 |
| 5,223,482 | 6/1993 | Schilling | 514/12 |
| 5,234,814 | 8/1993 | Card | 435/7.21 |
| 5,246,944 | 9/1993 | Greenlee | 514/312 |
| 5,260,210 | 11/1993 | Rubin | 435/240.23 |
| 5,270,165 | 12/1993 | Van Nostrand | 435/7.1 |

FOREIGN PATENT DOCUMENTS

| | | |
|---|---|---|
| 0218440 | 4/1987 | European Pat. Off. . |
| 0457295A2 | 11/1991 | European Pat. Off. . |

OTHER PUBLICATIONS

Ishi, Tsuyoshi (1969) "Enzyme Histochemical Studies of Senile Plaques and the Plaque–Like Degeneration of Arteries and Capillaries (Scholz)", *Acta neuropath.* 14:250–260.

Op Den Velde, W. et al. (1976) "Some Cerebral Proteins and Enzyme Systems in Alzheimer's Presenile and Senile Dementia", *Journal of the American Geriatrics Society*, XXIV(1):12–16.

Kawai, Mitsuru, et al. (1992) "Subcellular Localization of Amyloid Precursor Protein in Senile Plaques of Alzheimer's Disease", *American Journal of Pathology*, 140(4):947–958.

Armbruster, David A., et al. (1988) "The regional variability of enzymes in the brain: relevance to CSF enzyme determinations", *Clinica Chimica Acta*, 175:227–238.

Kraus, Arthur S., et al. (1992) "Aluminum, Fluoride and the Prevention of Alzheimer's Disease", *Canadian Journal of Public Health*, 83 (2):97–100.

Sofic, E., et al. (1991) "Biochemical Membrane Constituents and Activities of Alkaline and Acid Phosphatase and Cathepsin in Cortical and Subcortical Brain Areas in Dementia of the Alzheimer Type", *Dementia*, 2:39–44.

Ohmar, Rawhi, et al. (1993) "Acid Phosphatase Activity in Senile Plaques and Cerebrospinal Fluid of Patients with Alzheimer's Disease", *Arch Pathol Lab Med*, 117:166–169.

Shimohama, Shun, et al. (1993) "Reduction of Low–Molecular–Weight Acid Phosphatase Activity in Alzheimer Brains", *Ann Neurol* 33:616–621.

Rush, D. N., et al. (1980) "The Effect of Levamisole In Experimental Murine Amyloidosis", *Journal of Immunopharmacology*, 2(4):553–565.

*Primary Examiner*—Brian Burn
*Attorney, Agent, or Firm*—Townsend and Townsend and Crew LLP

[57] ABSTRACT

The present invention provides a method of inhibiting β-amyloid toxicity in brain cells. The method includes administering to the cells an amount of an alkaline phosphatase inhibitor which is pharmacologically effective to reduce degeneration in the cells. Methods of treatment of peripheral neuropathy are also provided using acid or alkaline phosphatase inhibitors.

19 Claims, 5 Drawing Sheets

ALKALINE AND ACID PHOSPHATASE INHIBITORS IN TREATMENT OF NEUROLOGICAL DISORDERS

CROSS-REFERENCE TO RELATED APPLICATION

This application is a continuation-in-part of U.S. Ser. No. 08/071,281, filed Jun. 1, 1993 (now abandoned).

FIELD OF THE INVENTION

The present invention relates to the use of alkaline and acid phosphatase inhibitors in the treatment of neurological disorders. More particularly, the present invention relates to the use of various specific phosphatase inhibitors in the treatment of β-amyloid toxicity in brain cells and the use of phosphatase inhibitors in the treatment of peripheral neuropathy.

BACKGROUND OF THE INVENTION

Alzheimer's Disease (AD) is a progressive neurodegenerative condition affecting a substantial proportion of people over the age of 65. There is presently no known cure. One hallmark of AD neuropathology includes neurofibrillary tangles involving neuronal processes and closely associated with gliotic astrocytes and with macrophages. Another hallmark of AD is the presence in the brain of affected individuals of "plaques" composed of a variety of proteins, glycoproteins, and other components. These plaques always contain a high proportion of β-amyloid peptide, a 42–43 amino acid peptide aberrantly cleaved from the amyloid precursor protein.

Though normally observed in blood and cerebrospinal fluid, β-amyloid peptide in an aggregated form is considered partly responsible for the noted neuronal death observed in AD (Koh, et al., Brain Res. 533:315 (1990); Mattson, et al., J. Neurosoi, 12:376 1992, etc.). Exposure of brain cells cultured in vitro to β-amyloid peptide results in the degeneration of these cells. How this aggregated peptide mediates neuronal death is unclear, yet published reports suggest a programmed cell death or apoptotic mechanism. Loo, et al., PNAS, 90:7951 (1993).

Neuronal death found in AD involves the loss of specific neuronal subtypes, possibly by the aforementioned mechanism of programmed cell death/apoptosis (PCD), an active suicide program that differs markedly from necrotic death (Loo, et al., PNAS 90:7951, 1993). The mechanism of programmed cell death induction in neurons is unclear, yet measurable/observable characteristics of PCD exist. Examples of changes observed during the process of PCD are chromatin condensation or margination, synthesis of required death proteins, DNA fragmentation into repeating 200 bp units. Increases in certain transcription and translation products that precede the programmed death are also observed.

Other amyloidogenic diseases exist that are associated with β-amyloid. These include Downs Syndrome and Hereditary Cerebral Hemorrhage with Amyloidosis-Dutch Type (HCHWA-D).

Alkaline phosphatases are a family of enzymes which serve diverse functions in mammalian cells. The major activity of these enzymes is to remove phosphate from nucleotides, and the 5' nucleotidases are included in this family. While specific chemical reactions catalyzed by these enzymes are well characterized, their role in cellular metabolism and regulation is less clearly defined.

Levamisole is an alkaline phosphatase inhibitor sold commercially under the brand name "Ergamisol" by Janssen Pharmaceutica of Piscataway, N.J. This product is available in tablets of levamisole hydrochloride for oral administration that contain the equivalent of 50 mg of levamisole base. Levamisole has been used in the treatment of colon cancer. Recommended dosage for treatment of colon cancer is 50 mg every eight hours for three days.

Acid phosphatases are another family of enzymes that serve diverse functions in mammalian cells.

European patent Application No. 91107844.2, Publication No. 0457295A2, purports to disclose the use of protein phosphatase inhibitors, such as okadaic acid, calyculin-A and vanadate for the treatment of amyloidosis associated with AD.

SUMMARY OF THE INVENTION

The present invention relates to the finding that arylimidothiazole derivative inhibitors of alkaline phosphatase can reduce neuronal death induced by β-amyloid peptide.

In a first aspect, the present invention is a method of inhibiting β-amyloid toxicity in brain cells. This method includes administering to the cells an amount of an arylimidothiazole derivative having alkaline phosphatase inhibitory activity effective to reduce cell degeneration. The brain cells can be located in a living organism suffering from an amyloidogenic neurologic disorder, such as Alzheimer's Disease (AD). The brain cells can also be located in a living organism suffering from other amyloidogenic diseases, such as Downs Syndrome or Hereditary Cerebral Hemorrhage with Amyloidosis-Dutch Type (HCHWA-D). The brain cells can also be located in vitro. In a preferred embodiment, the arylimidothiazole derivative is administered orally, intravenously, intraperitoneally, intramuscularly, by injection into cerebrospinal fluid, by injection into an intracerebral ventricle, or via a carrier protein. The arylimidothiazole derivative is preferably administered at a dose of from approximately 0.01 mg/kg to 10 mg/kg body weight per day, more preferably less than 5 mg/kg. Preferred arylimidothiazole derivatives include levamisole, bromolevamisole, and bromotetramisole.

In a second aspect, the invention is a method of treating a human subject having a peripheral neuropathy. This method includes administering to the subject an amount of an alkaline phosphatase inhibitor which is pharmacologically effective to alleviate the symptoms of the peripheral neuropathy. The alkaline phosphatase inhibitor can be administered in any of a variety of ways, including orally, intravenously, intraperitoneally, or intramuscularly. Preferred alkaline phosphatase inhibitors for this aspect of the invention are arylimidothiazole derivatives, such as levamisole, bromolevamisole and bromotetramisole. The alkaline phosphatase inhibitor is preferably administered at a dose of from approximately 0.001 mg/kg to 10 mg/kg body weight per day, more preferably less than 5 mg/kg.

In a third aspect the invention is a method of treating a human subject having a peripheral neuropathy. This method includes administering to the subject an amount of an acid phosphatase inhibitor which is pharmacologically effective to alleviate the symptoms of the peripheral neuropathy. The acid phosphatase inhibitor can be administered in any of a variety of ways, including orally, intravenously, intraperitoneally, or intramuscularly. Preferred acid phosphatase inhibitors for this aspect of the invention are para-chloromercuribenzoate (pCMB) and inorganic salts of tartrate or fluoride. Preferred inorganic salts for this aspect of the invention are Na; K; and Na,K. The acid phosphatase inhibitor is preferably administered at a dose of from approximately 0.001 mg/kg to 10 mg/kg body weight per day.

DETAILED DESCRIPTION OF THE INVENTION

The present invention relates to the use of alkaline phosphatase inhibitors or acid phosphatase inhibitors as therapeutic agents for neurological disorders, such as Alzheimer's Disease (AD) and peripheral neuropathies.

It is one of the surprising discoveries of the present invention that arylimidothiazole derivatives having alkaline phosphatase inhibitory activity can be used to inhibit the death of neurons due to β-amyloid peptide toxicity.

A number of different approaches can be taken to the inhibition of alkaline phosphatases. For example, they can be inhibited by arylimidothiazole compounds such as levamisole, which is specific for mammalian alkaline phosphatase, or by compounds that complex active Zn ion, which is required for alkaline phosphatase activity. Chemical inhibitors include, but are not limited to, levamisole ( (−)-(S)-2,3,5,6-tetrahydro-6-phenylimidoazide [2, 1-b]thiazole monohydrochloride), bromolevamisole, bromotetramisole, other arylimidothiazole derivatives, and the like. Still other alkaline phosphatase inhibitors include 1,10 phenanthroline, phenylalanine, IBMX, purines, and theophylline.

The presence of β-amyloid in AD and other amyloidogenic proteins is associated not only with deposition of amyloid in plaques, but also with neurotoxicity associated with this peptide. Thus, prevention of this neurotoxicity is an important goal of the present invention. We have surprisingly discovered that arylimidothiazole derivatives having alkaline phosphatase inhibitory activity can attenuate or prevent such neurotoxicity.

Another aspect of the present invention involves administration of acid phosphatase inhibitors to patients with peripheral neuropathies.

A number of different approaches can be taken to the inhibition of acid phosphatases. Acid phosphatase can be inhibited by chemical compounds, such as para-chloromercuribenzoate (pCMB) or inorganic salts of tartrate and fluoride. Preferred inorganic salts include Na; K; and Na,K.

One aspect of the present invention involves administration of inhibitors of alkaline phosphatase to patients with an amyloidogenic disease associated with β-protein, including AD, Downs Syndrome and HCHWA-D, as well as administration to patients suspected of having these diseases, particularly AD.

Alzheimer's Disease can be diagnosed by any number of traditional diagnostic criteria such as psychometrics that assess, for example, cognitive function, intelligence, language, memory, visual-spatial skills, and frontal lobe skills, or by neuropathological criteria such as immunological markers, enzyme assay, or CAT scan.

The invention can also be used prophylactically for those patients at risk for the development of AD or other amyloidogenic disease. Such patients can be identified through family histories or through a biochemical or immunological test indicative of such diseases. An example of an immunological test for AD involves the use of an antibody for the amyloid precursor protein (APP) in the CSF of a patient suspected of having AD. In this test, low levels of APP compared to normal levels are indicative of AD. See Van Nostrand et al., *Science*, 256:1279 (1992).

The administration of alkaline phosphatase inhibitors to prevent β-amyloid peptide toxicity can be by any of a number of methods known to those skilled in the art. Such methods include the delivery of the inhibitor orally or through intravenous, intraperitoneal, or intramuscular injection. Other known methods include techniques for administering compounds directly into the central nervous system (CNS), such as injection into cerebrospinal fluid, injection into an intracerebral ventricle, or by a carrier protein that actively transports the inhibitor to the brain. Administration of alkaline or acid phosphatase inhibitors for treatment of peripheral neuropathies can be by any of the foregoing; however, such treatment generally does not involve administration into the CNS.

Preferred dosage range when using chemical inhibitors can be determined using techniques known to those having ordinary skill in the art. For levamisole, dosages of 0,001 mg/kg to 10 mg/kg body weight per day for an average adult, more preferably less than 5 mg/kg, are believed to be effective in the treatment of AD. For some patients daily doses of an alkaline phosphatase inhibitor is required for optimum relief. For other patients relief can be achieved with every other day, or even weekly administration.

It is known that cultured rat hippocampal neurons are killed by the application of β-amyloid peptides. Thus, prevention of neurotoxicity can be shown as an inhibition in death of these neurons. Selection of appropriate alkaline phosphatase inhibitors for use in inhibitors of β-amyloid toxicity can thus be made through use of a model system making use of hippocampal neurons in the presence of β-amyloid peptides. Compounds that prevent death of these neurons in this system are likely to have significant activity in inhibition of β-amyloid toxicity.

The effect of treatment with alkaline phosphatase inhibitors on neurons exposed to β-amyloid peptide was tested in two experiments, described below in Examples 1 and 2.

EXAMPLE 1

Inhibition of β-amyloid Peptide Toxicity by Alkaline Phosphatase Inhibitors

HT4 neurotumor cells were treated with 50 μM β-amyloid peptide 25–35 and 250 μM quisqualate. The cells were also treated with 100 μM of the following alkaline phosphatase inhibitors: 1,10 phenanthroline, phenylalanine, IBMX, bromotetramisole, purine, and theophylline. The death of the neurons was determined by measuring LDH activity in the media 24 hours after treatment. The release of LDH from the cells into the surrounding media indicates cell death.

Figure 1:
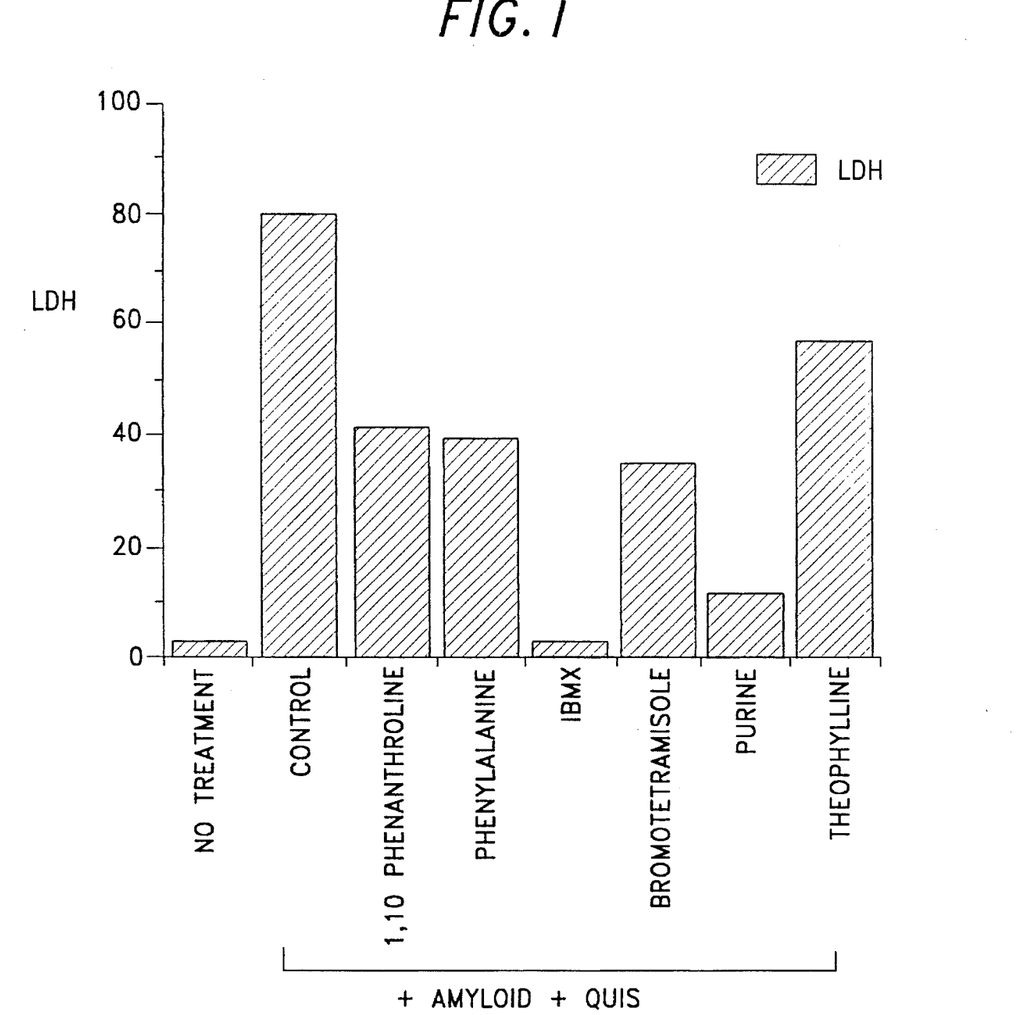
FIG. 1 graphically depicts the effect of alkaline phosphatase inhibitors on rat brain neurotumor cells treated with β-amyloid peptide.

FIG. 1 illustrates the results of the study of Example 1. Control cells, treated only with β-amyloid peptide and quisqualate, showed a high LDH activity 24 hours after treatment, indicating a high degree of cell death. Cells subjected to no treatment had only a low level of LDH activity. The addition of alkaline phosphatase inhibitors significantly reduced the amount of LDH activity and therefore inhibited the death of neuronal cells due to exposure to β-amyloid peptide, IBMX appeared to be the most effective compound tested in inhibiting cell death from amyloid toxicity.

EXAMPLE 2

Inhibition of β-amyloid Peptide Toxicity by Levamisole

To further determine the effect of alkaline phosphatase inhibitors on βamyloid peptide toxicity, rat embryonic hippocampal neurons in culture were exposed to 50 μM β-amyloid 25–35 in the presence of levamisole concentrations of 250 μM and 500 μM.

Figure 2:
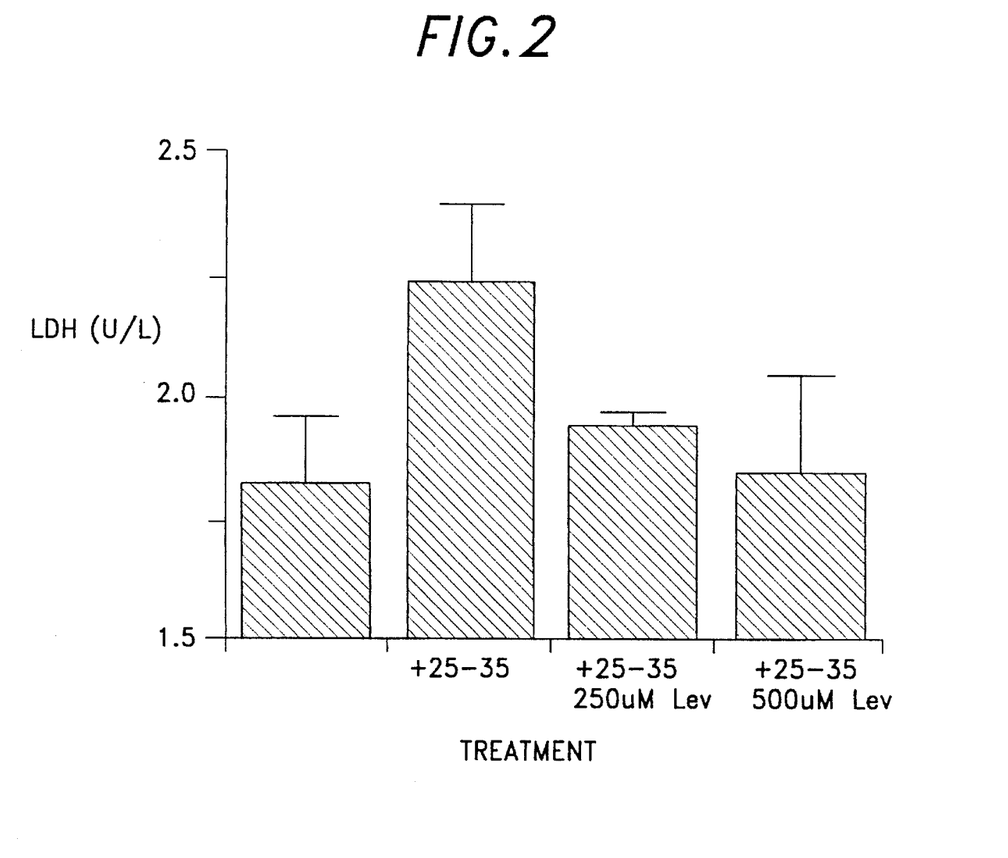
FIG. 2 graphically depicts the effect of levamisole on primary cultures of rat embryonic hippocampal neurons exposed to β-amyloid peptide.

The results of the experiment of Example 2 are illustrated in FIG. 2. The death of the neurons, as indicated by the release of LDH from the cells, was reduced by the presence of levamisole at a concentration of 250 μM. LDH activity was also reduced by the presence of levamisole at a concentration of 500 μM.

Example 2 demonstrates that death of neuronal cells due to exposure to βamyloid peptide is reduced by the presence of levamisole.

As mentioned earlier, the prior art indicates that okadaic acid may be useful in the treatment of amyloidosis associated with Alzheimer's Disease. The experiment of Example 3 below, however, illustrates that okadaic acid causes hippocampal neuronal injury upon administration with β-amyloid.

EXAMPLE 3

Okadaic Acid Causes Hippocampal Neuronal Injury Upon Administration with β-Amyloid Hippocampal neurons were treated with 50 μM β-amyloid (β25–35) and 50 nM okadaic acid for 24 hours in Dulbeccois Modified Eagle's (DME) medium at 37° C. Following the 24-hour treatment period, an aliquot of media was removed for determination of LDH efflux from the neurons, which is an indicator of cell death. Each bar in FIG. 3, except the bar representing okadaic acid alone, represents the mean of 4 wells ± the standard deviation. The bar representing okadaic acid alone represents the mean of 2 wells ± the standard deviation.

Figure 3:
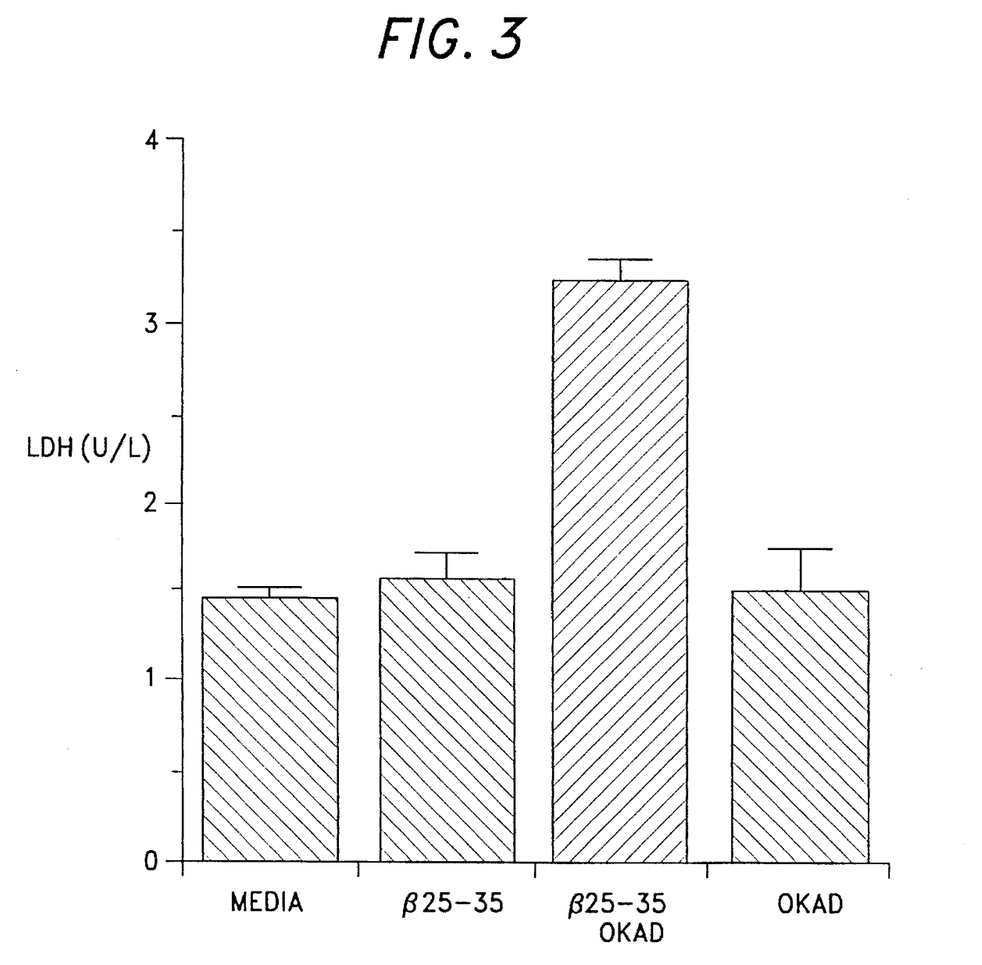
FIG. 3 graphically depicts the effect of okadaic acid on hippocampal neurons treated with β-amyloid peptide.

FIG. 3 illustrates that okadaic acid causes hippocampal neuronal injury upon administration with β-amyloid. This finding is particularly surprising in light of the prior art, wherein okadaic acid is indicated as being useful for the treatment of amyloidosis associated with Alzheimer's Disease.

The effect of different alkaline phosphatase inhibitors are compared below in Example 4.

EXAMPLE 4

Inhibition of Porcine Kidney and Calf Intestinal Alkaline Phosphatase

Figure 4:
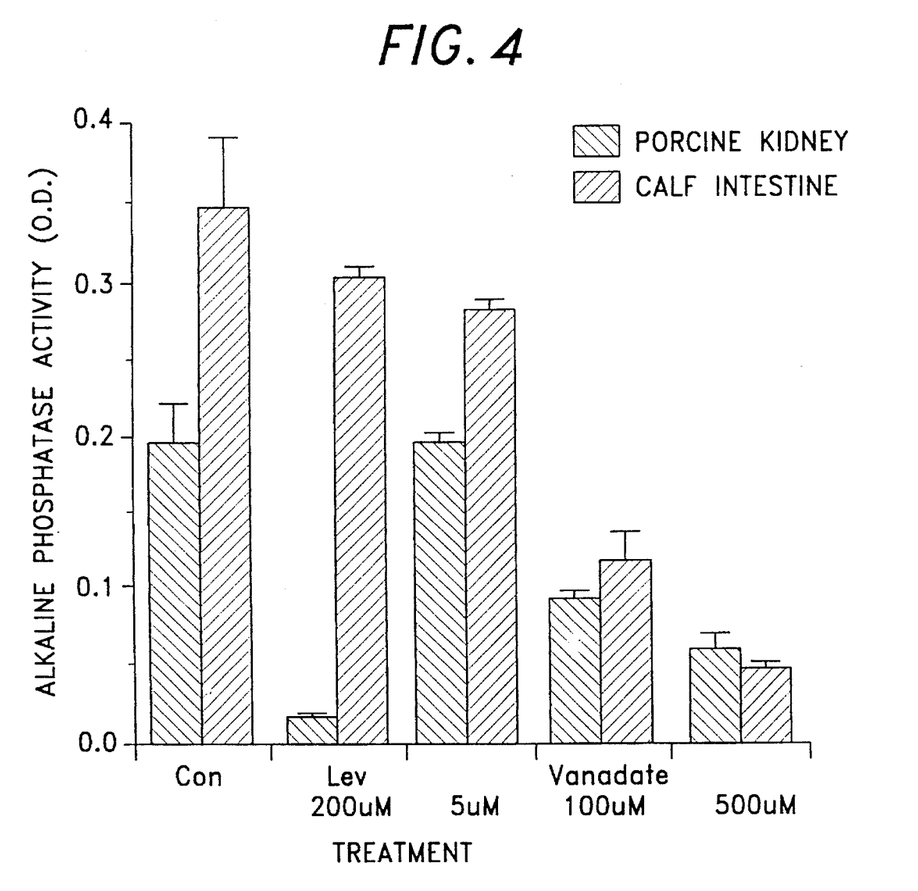
FIG. 4 graphically depicts the effect of levamisole or vanadate on alkaline phosphatase activity from porcine kidney and from calf intestine.

Porcine kidney (0.01 U) and calf intestinal (0.002 U) alkaline phosphatases were assayed in the presence of levamisole (200 μM) or vanadate salt (5–500 μM) using pNPP (5 mM) as substrate. The assay was carried out in pH 5.5 lysis buffer. Each bar in FIG. 4 represents the mean of quadruplicates ± the standard deviation. The results of the experiment of Example 4 are illustrated in FIG. 4. Both levamisole and vanadate appear to inhibit porcine kidney alkaline phosphatase activity from porcine kidney and calf intestine. Inhibition of porcine kidney alkaline phosphatase activity is unexpectedly high in the presence of levamisole. Vanadate at 100 μM significantly inhibited calf intestinal alkaline phosphatase, while levamisole at 200 μM had little effect. The effect of treatment on humans with AD using arylimidothiazole derivatives having alkaline phosphatase inhibitory activity is described below in Examples 5–9.

EXAMPLE 5

Oral Treatment of AD with Arylimidothiazole Derivatives

Human subjects diagnosed as suffering from AD are administered 50 mg of an arylimidothiazole derivative, such as levamisole, orally every eight hours for three days. The treatment is repeated every 14 days for a period of 6 months. With treatment, the symptoms of AD in the subject are lessened, as the subject experiences improved memory and cognitive skills.

EXAMPLE 6

Intravenous Treatment of AD with Arylimidothiazole Derivatives

Human subjects diagnosed as suffering from AD are administered 0.5 mg/kg arylimidothiazole derivatives intravenously once or twice daily for four days. This administration is repeated every 14 days for a period of 4 months.

EXAMPLE 7

Treatment of AD with Levamisole

A human patient diagnosed as suffering from Alzheimer's Disease is administered about 50 mg levamisole orally every eight hours for three days. The treatment is repeated every 14 days for a period of 6 months. The symptoms of AD in the patient are lessened, as the patient experiences improved memory and cognitive skills.

EXAMPLE 8

Continuous Treatment of AD with Arylimidothiazole Derivatives

Human subjects diagnosed as suffering from AD are administered 0.05 mg/kg of an arylimidothiazole derivative, such as levamisole, orally every day for a period of six months. With treatment, the symptoms of AD in the patient decrease and deterioration stops shortly after initiation of treatment.

EXAMPLE 9

Continuous Treatment of AD with Levamisole

A human patient diagnosed as suffering from Alzheimer's Disease is identified as having deteriorating symptoms of the disease. The patient is administered about 10 mg levamisole orally once per day for a period of six months. With treatment, the symptoms of AD in the patient decrease and deterioration stops shortly after initiation of treatment.

As discussed above, the present invention includes the treatment of peripheral neuropathies, such as chemotherapeutic induced neuropathy, and neurophathies caused by diabetes and other degenerative disease states. In the context of this aspect of the invention, both acid and alkaline phosphatase inhibitors are effective. Exemplary inhibitors in this regard include Na, K-tartrate, NaF, calyculin-A, vanadate and the arylimidothiazole derivatives. Identification of appropriate protein phosphatase inhibitors can be conducted through a model system making use of dorsal root ganglion cells treated with Nerve Growth Factor (NGF) and vinblastine. Effective compounds in this system result in an increased percentage of cell viability in the presence of vinblastine.

The effect of treatment with Na, K-tartrate on dorsal root ganglion cells treated with Nerve Growth Factor and vinblastine was tested and is described below in Example 10.

EXAMPLE 10

Inhibition of Vinblastine-Induced Toxicity by Na,K-Tartrate

Dorsal root ganglion cells were treated with Nerve Growth Factor (NGF) (50 ng/ml), vinblastine (500 nM) and Na,K-tartrate (500 µM) for 24 hours. Following the treatment, the dorsal root ganglion cells were stained with ethidium bromide and fluorescein diacetate to stain dead and live cells, respectively.

Figure 5:
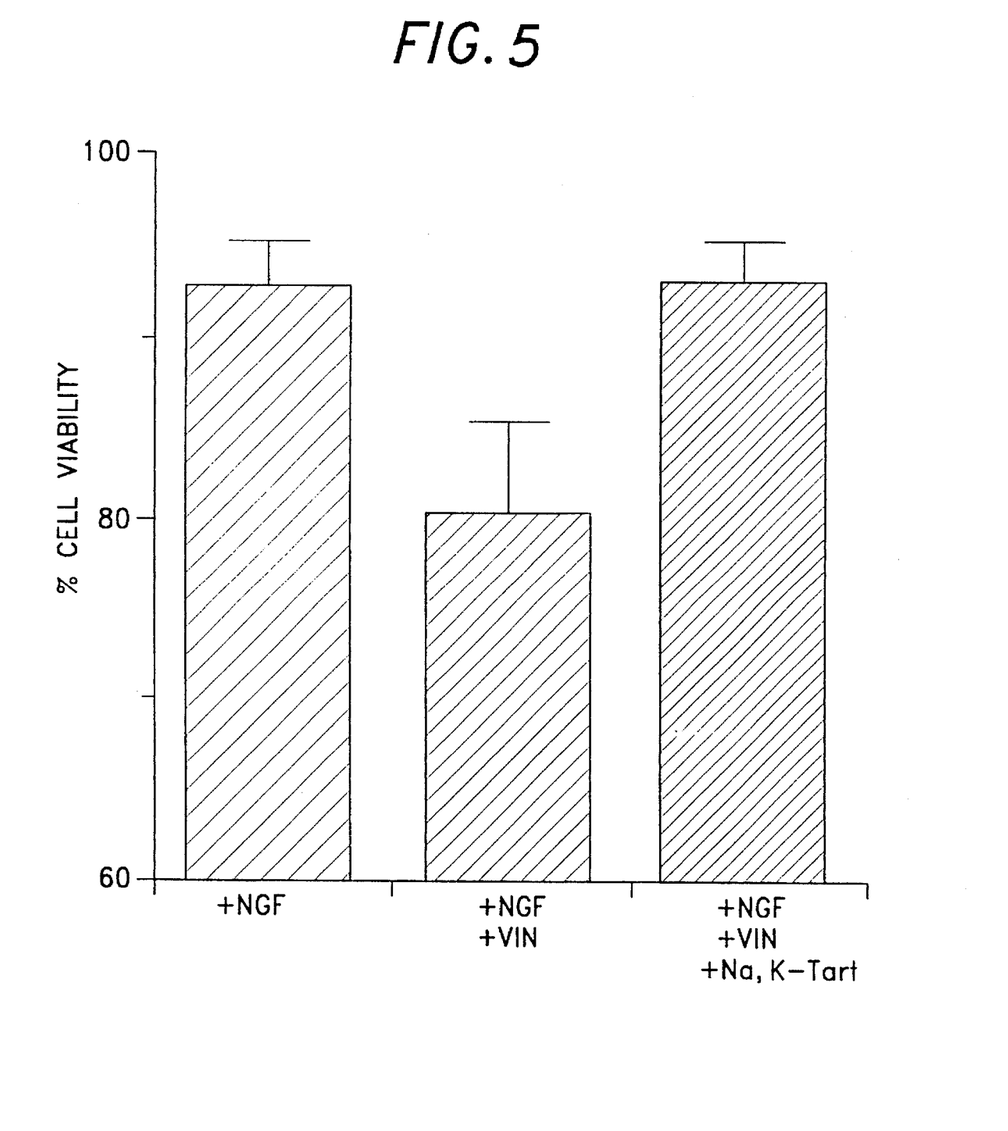
FIG. 5 graphically depicts the effect of Na,K-tartrate on dorsal root ganglion cells treated with Nerve Growth Factor and vinblastine.

FIG. 5 illustrates the results of the study of Example 16. Percentage cell viability is determined from the ratio of live cells to total cell number. Each bar in FIG. 7 represents the mean of 3 wells ± the standard deviation. Control cells, treated only with NGF, showed a high degree of cell viability. Cells exposed to NGF and vinblastine showed a decrease in cell viability. The addition of Na,K-tartrate significantly increased the percentage cell viability in the presence of vinblastine.

The effect of treatment on humans with peripheral neuropathy using either alkaline or acid phosphatase inhibitors is described below in Examples 11-14.

EXAMPLE 11

Treatment of Chemotherapeutic-Induced Peripheral Neuropathy with Acid Phosphatase Inhibitors Human subjects with peripheral neuropathy caused by chemotherapeutic agents such as vinblastine, vincristine, or taxol are administered 10 mg/kg of an acid phosphatase inhibitor. The acid phosphatase inhibitor is administered orally or systemically to these subjects once or twice a day for two days prior to and four days following the administration of the chemotherapeutic regimen. Following treatment, an assessment of motor coordination and peripheral paresthesia is made, as specified by those skilled in the art.

EXAMPLE 12

Treatment of Nonchemotherapeutic-Induced Peripheral Neuropathy with Acid Phosphatase Inhibitors Human subjects with peripheral neuropathy caused by diabetes or other degenerative disease states are administered 5 mg/kg of an acid phosphatase inhibitor twice per day for a period of 6 months. Following treatment, an assessment of motor coordination and peripheral paresthesia is made, as specified by those skilled in the art.

EXAMPLE 13

Treatment of Chemotherapeutic-Induced Peripheral Neuropathy with Alkaline Phosphatase Inhibitors Human subjects with peripheral neuropathy caused by chemotherapeutic agents such as vinblastine, vincristine, or taxol are administered 5 mg/kg of levamisole. The alkaline phosphatase inhibitor is administered orally or systemically to these subjects once or twice a day for two days prior to and four days following the administration of the chemotherapeutic regimen. Following treatment, an assessment of motor coordination and peripheral paresthesia is made, as specified by those skilled in the art.

EXAMPLE 14

Treatment of Nonchemotherapeutic-Induced Peripheral Neuropathy with Alkaline Phosphatase Inhibitors Human subjects with peripheral neuropathy caused by diabetes or other degenerative disease states are administered 5 mg/kg of an alkaline phosphatase inhibitor. The alkaline phosphatase inhibitor is administered orally or systemically to the subjects once or twice a day for two days prior to and four days following the administration of the chemotherapeutic regimen. Following treatment, an assessment of motor coordination and peripheral paresthesia is made, as specified by those skilled in the art. Although this invention has been described in terms of certain embodiments, these embodiments are set forth for illustrative purposes and are not intended to limit the scope of the invention. It will be apparent to those skilled in the art that various other modifications may be made to these embodiments without departing from the scope of the invention, which is properly determined upon reference to the following claims.

What is claimed is:

1. A method of inhibiting β-amyloid toxicity in brain cells exposed to β-amyloid peptide, comprising:

administering to said cells an arylimidothiazole derivative having nucleotide alkaline phosphatase inhibitory activity in an amount effective to reduce cell degeneration.

2. The method of claim 1, wherein said brain cells are located in a living organism suffering from a neurologic disorder.

3. The method of claim 2, wherein said neurologic disorder is Alzheimer's Disease.

4. The method of claim 1, wherein said brain cells are located in a living organism suffering from an amyloidogenic disease associated with β-amyloid protein.

5. The method of claim 4, wherein said amyloidogenic disease is Downs Syndrome or Hereditary Cerebral Hemorrhage with Amyloidosis-Dutch Type.

6. The method of claim 1, wherein said brain cells are located in vitro.

7. The method of claim 2, wherein the administering step comprises administering said arylimidothiazole derivative orally, intravenously, intraperitoneally, intramuscularly, by injection into cerebrospinal fluid, by injection into an intracerebral ventricle, or via a carrier protein.

8. The method of claim 2, wherein said arylimidothiazole derivative is administered at a dose of from approximately 0.01 mg/kg to 5 mg/kg body weight per day.

9. The method of claim 1, wherein said arylimidothiazole derivative is selected from the group consisting of levamisole, bromolevamisole and bromotetramisole.

10. A method of treating a human subject having a peripheral neuropathy, comprising:

administering to said subject an amount of a nucleotide alkaline phosphatase inhibitor which is pharmacologically effective to alleviate the symptoms of the peripheral neuropathy.

11. The method of claim 10, wherein the administering step comprises administering said alkaline phosphatase inhibitor orally, intravenously, intraperitoneally, or intramuscularly.

12. The method of claim 10, wherein said alkaline phosphatase inhibitor is administered at a dose of from approximately 0.001 mg/kg to 10 mg/kg body weight per day.

13. The method of claim 10, wherein said alkaline phosphatase inhibitor is an arylimidothiazole derivative.

14. The method of claim 13, wherein said arylimidothiazole derivative is selected from the group consisting of levamisole, bromolevamisole and bromotetramisole.

15. A method of treating a human subject having a peripheral neuropathy, comprising:

administering to said subject an amount of an acid phosphatase inhibitor which is pharmacologically effective to alleviate the symptoms of the peripheral neuropathy.

16. The method of claim 15, wherein the administering step comprises administering said acid phosphatase inhibitor orally, intravenously, intraperitoneally, or intramuscularly.

17. The method of claim 15, wherein said acid phosphatase inhibitor is administered at a dose of from approximately 0.001 mg/kg to 10 mg/kg body weight per day.

18. The method of claim 15, wherein said acid phosphatase inhibitor is para-chloromercuribenzoate (pCMB) or an inorganic salt of tartrate or fluoride.

19. The method of claim 18, wherein said inorganic salt is selected from the group consisting of Na; K; and Na,K.

* * * * *